United States Patent
Tate

(10) Patent No.: US 11,373,735 B2
(45) Date of Patent: Jun. 28, 2022

(54) RESULTS DEPENDENT ANALYSIS—ITERATIVE ANALYSIS OF SWATH DATA

(71) Applicant: DH TECHNOLOGIES DEVELOPMENT PTE. LTD., Singapore (SG)

(72) Inventor: Stephen A. Tate, Barrie (CA)

(73) Assignee: DH Technologies Development Pte. Ltd., Singapore (SG)

(*) Notice: Subject to any disclaimer, the term of this patent is extended or adjusted under 35 U.S.C. 154(b) by 742 days.

(21) Appl. No.: 16/315,592

(22) PCT Filed: Jun. 30, 2017

(86) PCT No.: PCT/IB2017/053982
§ 371 (c)(1),
(2) Date: Jan. 4, 2019

(87) PCT Pub. No.: WO2018/007921
PCT Pub. Date: Jan. 11, 2018

(65) Prior Publication Data
US 2019/0180848 A1  Jun. 13, 2019

Related U.S. Application Data

(60) Provisional application No. 62/359,189, filed on Jul. 6, 2016.

(51) Int. Cl.
*G16C 20/20* (2019.01)
*H01J 49/00* (2006.01)
*G16B 20/00* (2019.01)

(52) U.S. Cl.
CPC .......... *G16C 20/20* (2019.02); *H01J 49/0036* (2013.01); *H01J 49/0081* (2013.01); *G16B 20/00* (2019.02); *H01J 49/0031* (2013.01)

(58) Field of Classification Search
CPC .. G16C 20/20; H01J 49/0036; H01J 49/0081; H01J 49/0031; G16B 20/00; G01N 33/6848
(Continued)

(56) References Cited

U.S. PATENT DOCUMENTS

2006/0243900 A1* 11/2006 Overney ............ G01N 33/6848
                                                          250/284
2012/0049058 A1*  3/2012 Grothe, Jr. .......... H01J 49/0036
                                                          250/282
(Continued)

FOREIGN PATENT DOCUMENTS

WO        2015-056066 A1    4/2015

OTHER PUBLICATIONS

International Search Report and Written Opinion for PCT/IB2017/053982, dated Oct. 26, 2017.
(Continued)

*Primary Examiner* — Michael Maskell
(74) *Attorney, Agent, or Firm* — Kasha Law LLC; John R. Kasha; Kelly L. Kasha

(57) ABSTRACT

A plurality of measured product ion spectra are produced using a DIA tandem mass spectrometry method. One or more product ions are retrieved from a spectral library of known compounds or one or more theoretical product ions are calculated for the known compounds of a database. The one or more product ions or one or more theoretical product ions for each known compound are compared to the measured product ion spectra to identify one or more known compounds in the sample. A database of related known compounds is searched using one or more known compounds, producing one or more matching related compounds and one or more product ions for each related compound. The one or more product ions for each related compound are
(Continued)

compared to the measured product ion spectra to identify one or more related compounds in the sample.

9 Claims, 8 Drawing Sheets

(58) Field of Classification Search
USPC .................. 250/281, 282, 288; 702/27, 28
See application file for complete search history.

(56) References Cited

U.S. PATENT DOCUMENTS

| | | | |
|---|---|---|---|
| 2013/0206979 A1* | 8/2013 | Bonner | G16C 20/90 250/282 |
| 2015/0144778 A1* | 5/2015 | Bonner | H01J 49/0031 250/282 |
| 2016/0109424 A1* | 4/2016 | Johansen | G01N 30/7233 506/12 |

OTHER PUBLICATIONS

Mullard et al., "A New Strategy for MS/MS Data Acquisition Applying Multiple Data Dependent Experiments on Orbitrap Mass Spectrometers in Non-Targeted Metabolomic Applications," Metabolomics, 2015, vol. 11, No. 5, pp. 1068-1080.

Gillet et al. "Targeted Data Extraction of the MS/S Spectra Generated by Data-Independent Acquisition: A New Concept for Consistent and Accurate Proteome Analysis," Molecular & Cellular Proteomics, vol. 11, No. 6, Jun. 12, 2012, XP055471043, US, ISSN: 1535-9476, DOI: 10/1074/mcp.0111.016717.

* cited by examiner

RESULTS DEPENDENT ANALYSIS—ITERATIVE ANALYSIS OF SWATH DATA

CROSS REFERENCE TO RELATED APPLICATION

This application claims the benefit of U.S. Provisional Patent Application Ser. No. 62/359,189, filed Jul. 6, 2016, the content of which is incorporated by reference herein in its entirety.

INTRODUCTION

The teachings herein relate to iteratively analyzing tandem mass spectrometry or mass spectrometry/mass spectrometry (MS/MS) data. More particularly the teachings herein relate to systems and methods for automatically reanalyzing data collected from a data independent acquisition (DIA) tandem mass spectrometry method to confirm a hypothesis or identify a potential new hypothesis using information from one or more external sources.

BACKGROUND

A common problem in mass spectrometry is determining the identity of compounds present in a sample. In proteomics, for example, the problem is determining the identity of proteins present in the sample. Typically, compounds or proteins are identified or quantitated in a sample using a two-step tandem mass spectrometry process.

In the first step, experimental data is obtained. The proteins in a sample are digested using an enzyme such as trypsin, producing one or more peptides for each protein. Note that a peptide, as used herein, is a digested portion of a protein. Some proteins can be digested intact, so a peptide can also be the entire protein. However, in most cases peptides are digested portions of proteins.

The peptides digested from proteins are then separated from the sample over time using a sample introduction device or separation device. The separated peptides are then ionized using an ion source. The ionized peptides, or peptide precursor ions, are selected by mass-to-charge ratio (m/z), the selected precursor ions are fragmented, and the resulting product ions are mass analyzed using a tandem mass spectrometer. The result of the first step is a collection of one or more product ion mass spectra measured at one or more different times.

In the second step, information about known compounds or proteins expected to be in the experimental sample is obtained from A) stored spectral library or database or is B) insilico generated. This known data is compared to the experimental data. This known data includes, for example, mass-to-charge ratio values of product ions at specific retention times.

A) Information about product ions of known compounds, for example, can be obtained from a spectral library or database. A spectral library includes, for example, spectral data collected from analyzing each of the known compounds separately. Product ions from this previously collected spectral data are then compared to each of the one or more measured product ion mass spectra measured from a sample mixture at each of the one or more different times. Typically, known compounds are scored based through a range of methods which can include the use of spectral libraries or from correlation of signal of different fragment ions. The compounds in the sample mixture are then identified from the highest scoring known compounds.

B) Similarly, known proteins, for example, can be obtained from a database, and can be insilico digested using the same enzyme used in the tandem mass spectrometry experiment, producing one or more theoretical peptides for each known protein. Theoretical peptides are computationally fragmented, producing theoretical product ions for each insilico derived peptide. Theoretical retention times can also be calculated using a range of different approaches, i.e. SSRCalc (University of Manitoba), Grand Hydrophobicity measures etc. The resulting theoretical product ions are then compared to each of the one or more measured product ion mass spectra at each of the one or more different times. As above these insilico derived protein datasets, are scored based on how well their theoretical product ions match the one or more measured product ion mass spectra. The proteins in the sample are then identified from the highest scoring known proteins. As a result, known compounds or proteins in a sample mixture can be identified by comparing library or theoretical product ion m/z and retention time values to experimental product ion m/z and retention time values measured from the sample mixture.

The compounds or proteins identified in the sample through the use of either method described above are the result of the experiment. They are also used to provide or confirm a first or original hypothesis. Mass spectrometry experiments can be directed to many other original results or hypotheses, such as determining the quantity of known compounds or proteins in a sample. Generally, however, one mass spectrometry experiment is directed to one result or hypothesis. In order to determine or confirm another hypothesis about the sample requires performing an additional experiment which may include different sample collection and generation of additional data from the mass spectrometer. An additional experiment is necessary because most tandem mass spectrometry methods such as Single Reaction Monitoring, Parent Ion Monitoring, and Data Dependent Acquisition etc. do not provide enough data to determine or confirm multiple hypotheses.

Data independent tandem mass spectrometry methods, however, do provide a complete set of data for a mass-to-charge ratio m/z range that can be used to determine or confirm multiple hypotheses. Conventionally, however, methods are also used to determine or confirm a single hypothesis. The idea of using the same data to determine the validity of multiple hypotheses is known. Many researchers collect data on protein abundance change or straight identification of compounds in samples to try and develop a hypothesis for what is happening in the sample. This form of analysis requires methods which provide a completely unbiased analysis of the sample and an unbiased extraction of the data. As a result, systems and methods are needed to collect and automatically analyze DIA tandem mass spectrometry data to confirm or determine two or more hypotheses about a sample.

DIA is a tandem mass spectrometry method or workflow. In general, tandem mass spectrometry, or MS/MS, is a well-known technique for analyzing compounds. Tandem mass spectrometry involves ionization of one or more compounds from a sample, selection of one or more precursor ions of the one or more compounds, fragmentation of the one or more precursor ions into product ions, and mass analysis of the product ions.

Tandem mass spectrometry can provide both qualitative and quantitative information. The product ion spectrum can be used to identify a molecule of interest. The intensity of one or more product ions can be used to quantitate the amount of the compound present in a sample.

A large number of different types of experimental methods or workflows can be performed using a tandem mass spectrometer. Three broad categories of these workflows are, targeted acquisition, information dependent acquisition (IDA) or data dependent acquisition (DDA), and DIA.

In a targeted acquisition method, one or more transitions of a peptide precursor ion to a product ion are predefined for one or more proteins. As a sample is being introduced into the tandem mass spectrometer, the one or more transitions are interrogated during each time period or cycle of a plurality of time periods or cycles. In other words, the mass spectrometer selects and fragments the peptide precursor ion of each transition and performs a targeted mass analysis for the product ion of the transition. As a result, a mass spectrum is produced for each transition. Targeted acquisition methods include, but are not limited to, multiple reaction monitoring (MRM) and selected reaction monitoring (SRM).

IDA is a flexible tandem mass spectrometry method in which a user can specify criteria for performing targeted or untargeted mass analysis of product ions while a sample is being introduced into the tandem mass spectrometer. For example, in an IDA method a precursor ion or mass spectrometry (MS) survey scan is performed to generate a precursor ion peak list. The user can select criteria to filter the peak list for a subset of the precursor ions on the peak list. MS/MS is then performed on each precursor ion of the subset of precursor ions. A product ion spectrum is produced for each precursor ion. MS/MS is repeatedly performed on the precursor ions of the subset of precursor ions as the sample is being introduced into the tandem mass spectrometer.

In proteomics and many other sample types, however, the complexity and dynamic range of compounds is very large. This poses challenges for traditional targeted and IDA methods, requiring very high speed MS/MS acquisition to deeply interrogate the sample in order to both identify and quantify a broad range of analytes.

As a result, DIA methods have been used to increase the reproducibility and comprehensiveness of data collection from complex samples. DIA methods can also be called non-specific fragmentation methods. In a traditional DIA method, the actions of the tandem mass spectrometer are not varied among MS/MS scans based on data acquired in a previous precursor or product ion scan. Instead a precursor ion mass range is selected. A precursor ion mass selection window is then stepped across the precursor ion mass range. All precursor ions in the precursor ion mass selection window are fragmented and all of the product ions of all of the precursor ions in the precursor ion mass selection window are mass analyzed.

The precursor ion mass selection window used to scan the mass range can be very narrow so that the likelihood of multiple precursors within the window is small. This type of DIA method is called, for example, MS/MS$^{ALL}$. In an MS/MS$^{ALL}$ method a precursor ion mass selection window of about 1 amu is scanned or stepped across an entire mass range. A product ion spectrum is produced for each 1 amu precursor mass window. A product ion spectrum for the entire precursor ion mass range is produced by combining the product ion spectra for each mass selection window. The time it takes to analyze or scan the entire mass range once is referred to as one scan cycle. Scanning a narrow precursor ion mass selection window across a wide precursor ion mass range during each cycle, however, is not practical for some instruments and experiments.

As a result, a larger precursor ion mass selection window, or selection window with a greater width, is stepped across the entire precursor mass range. This type of DIA method is called, for example, SWATH acquisition. In SWATH acquisition the precursor ion mass selection window stepped across the precursor mass range in each cycle may have any width, or even larger. Like the MS/MS$^{ALL}$ method, all the precursor ions in each precursor ion mass selection window are fragmented, and all of the product ions of all of the precursor ions in each mass isolation window are mass analyzed. However, because a wider precursor ion mass selection window is used, the cycle time can be significantly reduced in comparison to the cycle time of the MS/MS$^{ALL}$ method.

U.S. Pat. No. 8,809,770 describes how SWATH acquisition can be used to provide quantitative and qualitative information about the precursor ions of compounds of interest. In particular, the product ions found from fragmenting a precursor ion mass selection window are compared to a database of known product ions of compounds of interest. In addition, ion traces or extracted ion chromatograms (XICs) of the product ions found from fragmenting a precursor ion mass selection window are analyzed to provide quantitative and qualitative information about an entire m/z range.

As described above, even though DIA methods, like SWATH acquisition, provide a complete set of data for an entire m/z range, to date these methods have not been used to determine or confirm multiple hypotheses. As a result, systems and methods are needed to collect and automatically analyze SWATH tandem mass spectrometry data to confirm or determine two or more hypotheses about a sample.

SUMMARY

A system is disclosed for identifying known compounds of a spectral library in a sample, automatically generating a list of related known compounds, and identifying related known compounds in the sample without reanalyzing the sample using a tandem mass spectrometry DIA method. A similar system is disclosed for identifying known compounds of a database of known compounds in a sample, automatically generating a list of related known compounds, and identifying related known compounds in the sample without reanalyzing the sample using a tandem mass spectrometry DIA method.

Both systems include a separation device, an ion source, a tandem mass spectrometer, and a processor. The separation device separates compounds from a sample over time. The ion source receives the plurality of compounds from the separation device and ionizes the plurality of compounds, producing an ion beam of precursor ions. The tandem mass spectrometer receives the ion beam from the ion source, divides an m/z range of the ion beam into two or more precursor ion mass selection windows, and selects and fragments the two or more precursor ion mass selection windows during each cycle of a plurality of cycles, producing a plurality of measured product ion spectra.

The processor receives the plurality of measured product ion spectra from the tandem mass spectrometer. In one system the processor retrieves from a spectral library of known compounds one or more product ions for each known compound. In the other system the processor retrieves a plurality of known compounds from a database. For each known compound of the database, the processor theoretically fragments the known compound, producing one or more theoretical product ions.

The processor compares the one or more product ions or the one or more theoretical product ions for each known compound to the measured product ion spectra to identify one or more known compounds in the sample. The processor searches a database of related known compounds using one or more known compounds, producing one or more matching related compounds and one or more product ions for each related compound. Finally, the processor compares the one or more product ions for each related compound to the measured product ion spectra to identify one or more related compounds in the sample.

Similarly, a method is disclosed for identifying known compounds of a spectral library in a sample, automatically generating a list of related known compounds, and identifying related known compounds in the sample without reanalyzing the sample using a tandem mass spectrometry DIA method. Another method is disclosed for identifying known compounds of a database of known compounds in a sample, automatically generating a list of related known compounds, and identifying related known compounds in the sample without reanalyzing the sample using a tandem mass spectrometry DIA method.

In both methods, a plurality of measured product ion spectra are received from a tandem mass spectrometer.

In one method, one or more product ions for each known compound are retrieved from a spectral library of known compounds. In the other method, a plurality of known compounds are retrieved from a database. For each known compound of the plurality of known compounds, the known compound is theoretically fragmented producing one or more theoretical product ions.

The one or more product ions or the one or more theoretical product ions for each known compound are compared to the measured product ion spectra to identify one or more known compounds in the sample. A database of related known compounds is searched using one or more known compounds, producing one or more matching related compounds and one or more product ions for each related compound. Finally, the one or more product ions for each related compound are compared to the measured product ion spectra to identify one or more related compounds in the sample.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
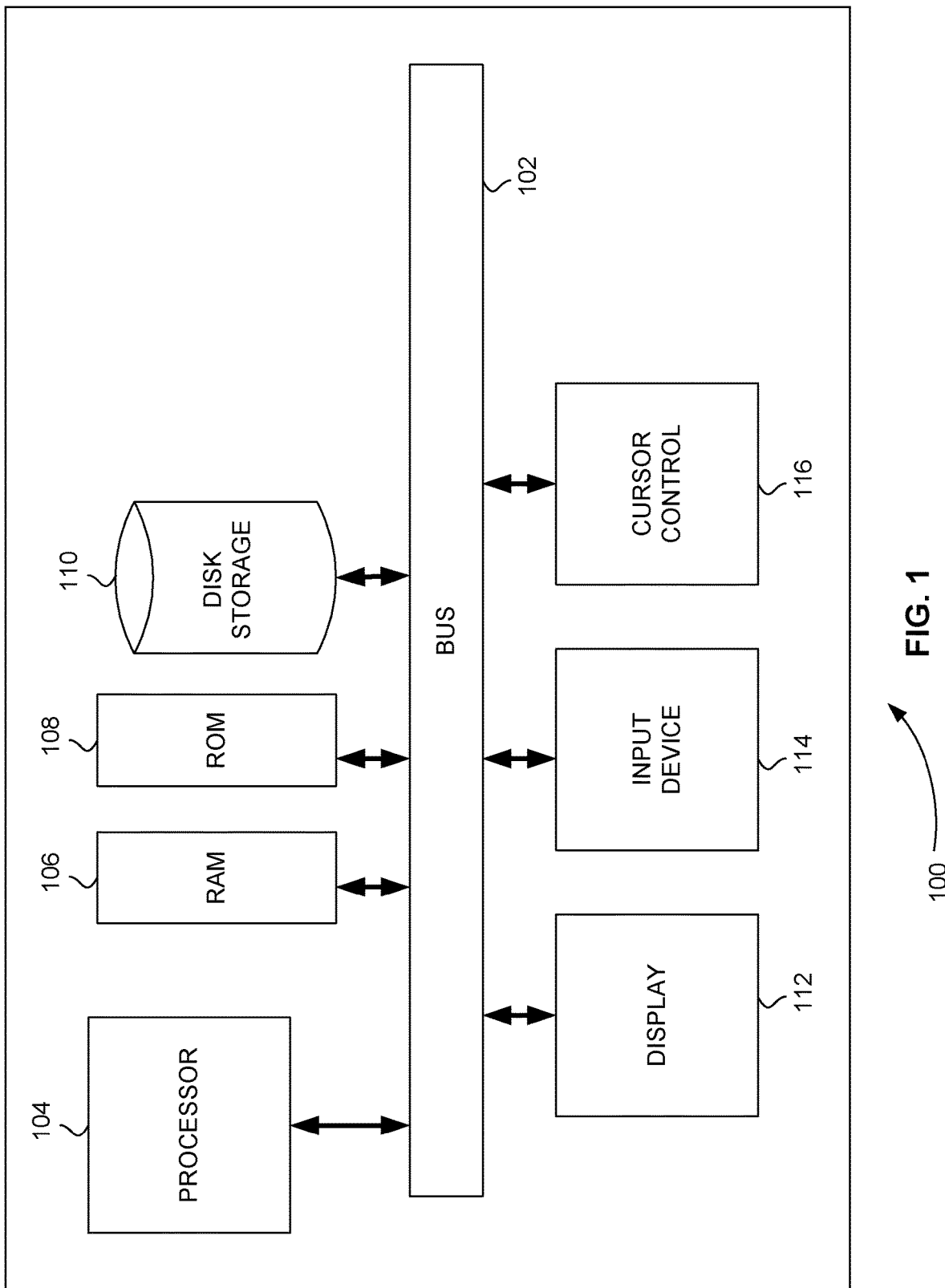
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Storage device 110 can also include more than one device. For example, storage device 110 can be part of an array or a data farm. In various embodiments, the data can be stored on one or more devices using many different techniques. For example, the data storage methods that are used can include, but are not limited to, a file system method, a relational database methods, object oriented database methods, index database methods, or data lake methods. A data lake is a method of storing data within a system that facilitates the colocation of data in variant schemas and structural forms, usually object blobs or files, for example. See https://en.wikipedia.org/wiki/Data_lake.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Result Dependent Analysis

As described above, even though data independent acquisition (DIA) methods, like SWATH acquisition, provide a complete set of data for an entire m/z range, to date these methods have not been used to determine or confirm multiple hypotheses. As a result, systems and methods are needed to collect and automatically analyze SWATH tandem mass spectrometry data to confirm or determine two or more hypotheses about a sample. Confirming or determine multiple hypotheses about a sample are generally done in series, for example.

In various embodiments, semantic searching is used to automatically analyze SWATH tandem mass spectrometry data to confirm or determine two or more hypotheses about a sample. In a first step, a first hypothesis that involves identifying or quantifying certain known compounds or proteins in a sample is confirmed or determined by performing a SWATH tandem mass spectrometry experiment. In a second step, the names of the known compounds or proteins identified or quantitated in the sample derive a new hypothesis that can come from searching external sources or from personal understanding of the system. Reprocessing the data with the second hypothesis that can provide evidence for this from the same SWATH tandem mass spectrometry data.

For example, a search against an external database can be used to find other proteins that may occur with the identified for a particular biological pathway/disease state, protein interaction network or any other source of biological reference. Or, for example, a search against an external database can be used to find modifications of known compounds or proteins identified or quantitated in the sample.

In either case, the SWATH tandem mass spectrometry data is analyzed again for the other proteins or modifications. As a result, the second hypothesis is confirmed or determined.

This use of semantic searching in SWATH tandem mass spectrometry provides a significant improvement over current systems and methods for analyzing a sample. First of all, the time it takes to confirm or determine multiple hypotheses about a sample is significantly reduced, because multiple experiments no longer have to be performed. Secondly, it allows multiple hypotheses to be confirmed or determined for samples that are available in only a limited quantity or for a limited time and, therefore, cannot be analyzed in multiple experiments.

This use of semantic searching in SWATH tandem mass spectrometry can be applied to many different workflows. One exemplary workflow is described in the following eight steps.

1) Extract a small number of proteins from samples that are defined from the interpretation of the original biological question (i.e. what proteins interact with CDK4 in response to a modification).

2) Confirm the presence of the proteins and their abundance changes across the experiments and analyze how this matches the experimental hypothesis.

3) If failed to match the experimental hypothesis, use correlations in the data to identify potential new hypothesis.

4) From new hypothesis extend the number of proteins to be extracted and retest new hypothesis.

S) If original hypothesis is confirmed extend data analysis by investigating the molecules which answer the hypothesis.

6) Include key modifications which may exist in each protein

7) Include alternate binding partners for each protein.

8) Re-extract and confirm the correlation of alternate binding proteins or modifications to the experiment.

The number of iterative types of analysis that can be performed are large and essentially allow for an expert system to be developed, which attempts to answer the experimental question in an automated manner. This provides only the key result to the end user based on the experiment which they are undertaking as well as allowing the researcher to extend their work.

Confirming or determining multiple hypotheses about a sample is possible because of the large amount of data present in each DIA experiment. DIA methods provide a larger amount of data than targeted acquisition methods like SRM, for example.

Figure 2:
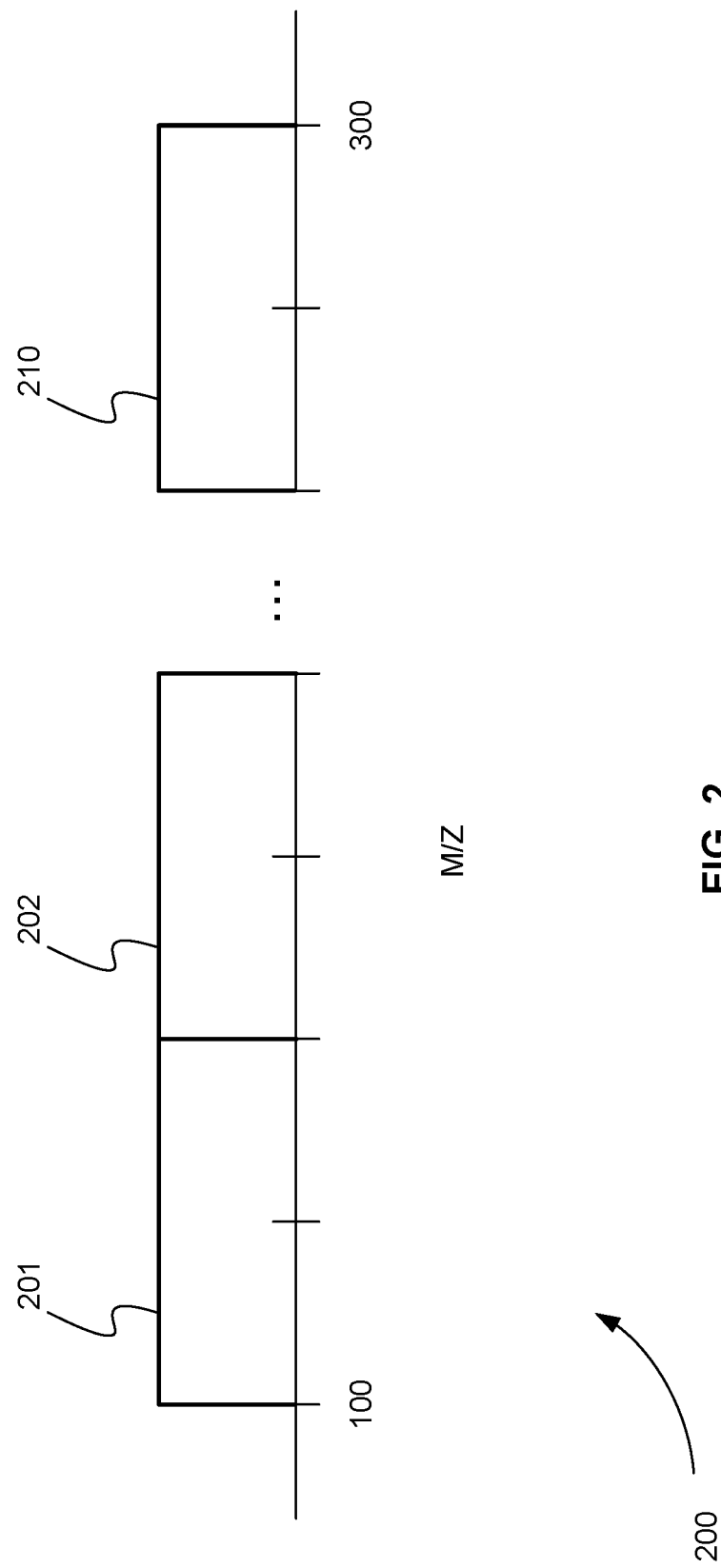
FIG. 2 is an exemplary diagram of a precursor ion mass-to-charge ratio (m/z) range that is divided into ten precursor ion mass selection windows for a data independent acquisition (DIA) workflow, in accordance with various embodiments.

FIG. 2 is an exemplary diagram 200 of a precursor ion mass-to-charge ratio (m/z) range that is divided into ten precursor ion mass selection windows for a data independent acquisition (DIA) workflow, in accordance with various embodiments. The m/z range shown in FIG. 2 is 200 m/z. Note that the terms "mass" and "m/z" are used interchangeably herein. Generally, mass spectrometry measurements are made in m/z and converted to mass by multiplying charge.

Each of the ten precursor ion mass selection or isolation windows spans or has a width of 20 m/z. Three of the ten precursor ion mass selection windows, windows 201, 202, and 210, are shown in FIG. 2. Precursor ion mass selection windows 201, 202, and 210 are shown as non-overlapping windows with the same width. In various embodiments, precursor ion mass selection windows can overlap and/or can have variable widths. U.S. Pat. No. 9,202,677 describes using overlapping precursor ion mass selection windows in a single cycle of SWATH acquisition, for example. U.S. Pat. No. 8,809,772 describes using precursor ion mass selection windows with variable widths in a single cycle of SWATH acquisition using variable precursor ion mass selection windows in SWATH acquisition, for example. In a conventional SWATH acquisition, each of the ten precursor ion mass selection windows is selected and then fragmented, producing ten product ion spectra for the entire m/z range shown in FIG. 2.

FIG. 2 depicts non-variable and non-overlapping precursor ion mass selection windows used in a single cycle of an exemplary SWATH acquisition. A tandem mass spectrometer that can perform a SWATH acquisition method can further be coupled with a sample introduction device. In proteomics, for example, the proteins of a sample are typically digested using an enzyme, such as trypsin before the sample is introduced into the tandem mass spectrometer. As a result, the sample introduction device separates one or more proteins digested proteins, or peptides, from the sample over time, for example. A sample introduction device can introduce a sample to the tandem mass spectrometer using a technique that includes, but is not limited to, injection, liquid chromatography, gas chromatography, capillary electrophoresis, or ion mobility. The separated one or more peptides are ionized by an ion source, producing an ion beam of precursor ions of the one or more proteins that are selected and fragmented by the tandem mass spectrometer.

As a result, for each time step of a sample introduction of separated proteins, each of the ten precursor ion mass selection windows is selected and then fragmented, producing ten product ion spectra for the entire m/z range. In other words, each of the ten precursor ion mass selection windows is selected and then fragmented during each cycle of a plurality of cycles.

Figure 3:
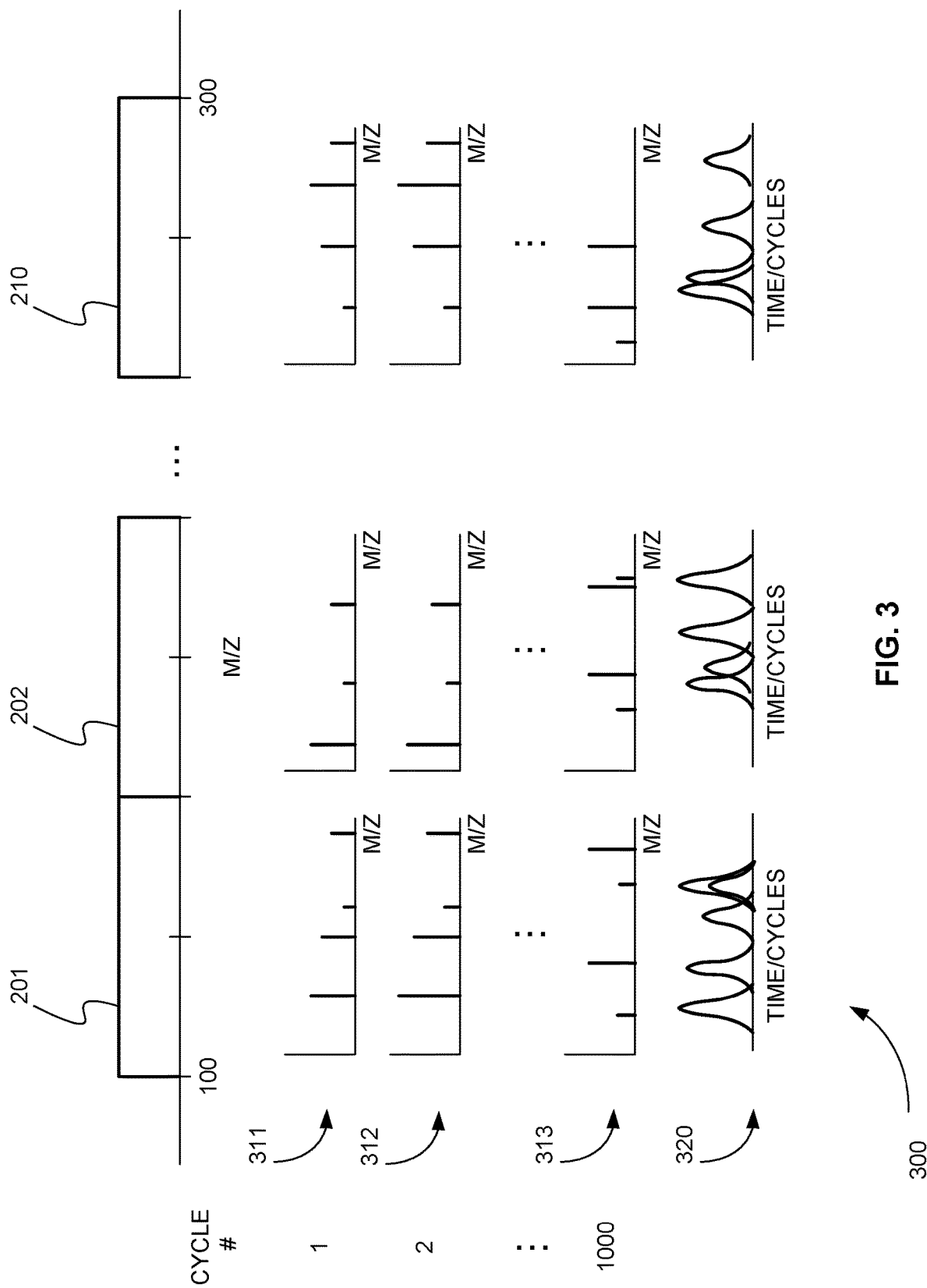
FIG. 3 is an exemplary diagram that graphically depicts the steps for obtaining product ion traces or XICs from each precursor ion mass selection window during each cycle of a DIA workflow, in accordance with various embodiments.

FIG. 3 is an exemplary diagram 300 that graphically depicts the steps for obtaining product ion traces or XICs from each precursor ion mass selection window during each cycle of a DIA workflow, in accordance with various embodiments. For example, ten precursor ion mass selection windows, represented by precursor ion mass selection windows 201, 202, and 210 in FIG. 3, are selected and fragmented during each cycle of a total of 1000 cycles.

During each cycle a product ion spectrum is obtained for each precursor ion mass selection window. For example, product ion spectrum 311 is obtained by fragmenting precursor ion mass selection window 201 during cycle 1, product ion spectrum 312 is obtained by fragmenting precursor ion mass selection window 201 during cycle 2, and product ion spectrum 313 is obtained by fragmenting precursor ion mass selection window 201 during cycle 1000.

By plotting the intensities of the product ions in each product ion spectrum of each precursor ion mass selection window over time, XICs are obtained for each precursor ion mass selection window. For example, XIC 320 is calculated from the 1,000th product ion spectra of precursor ion mass selection window 201. XIC 320 includes XIC peaks or traces for all of the product ions that are produced from fragmenting precursor ion mass selection window 201 during the 1000 cycles. Note that XICs can be plotted in terms of time or cycles.

XIC 320 is shown plotted in two dimensions in FIG. 3. However, each XIC of each precursor ion mass selection window is actually three-dimensional, because the different XIC peaks represent different m/z values.

Figure 4:
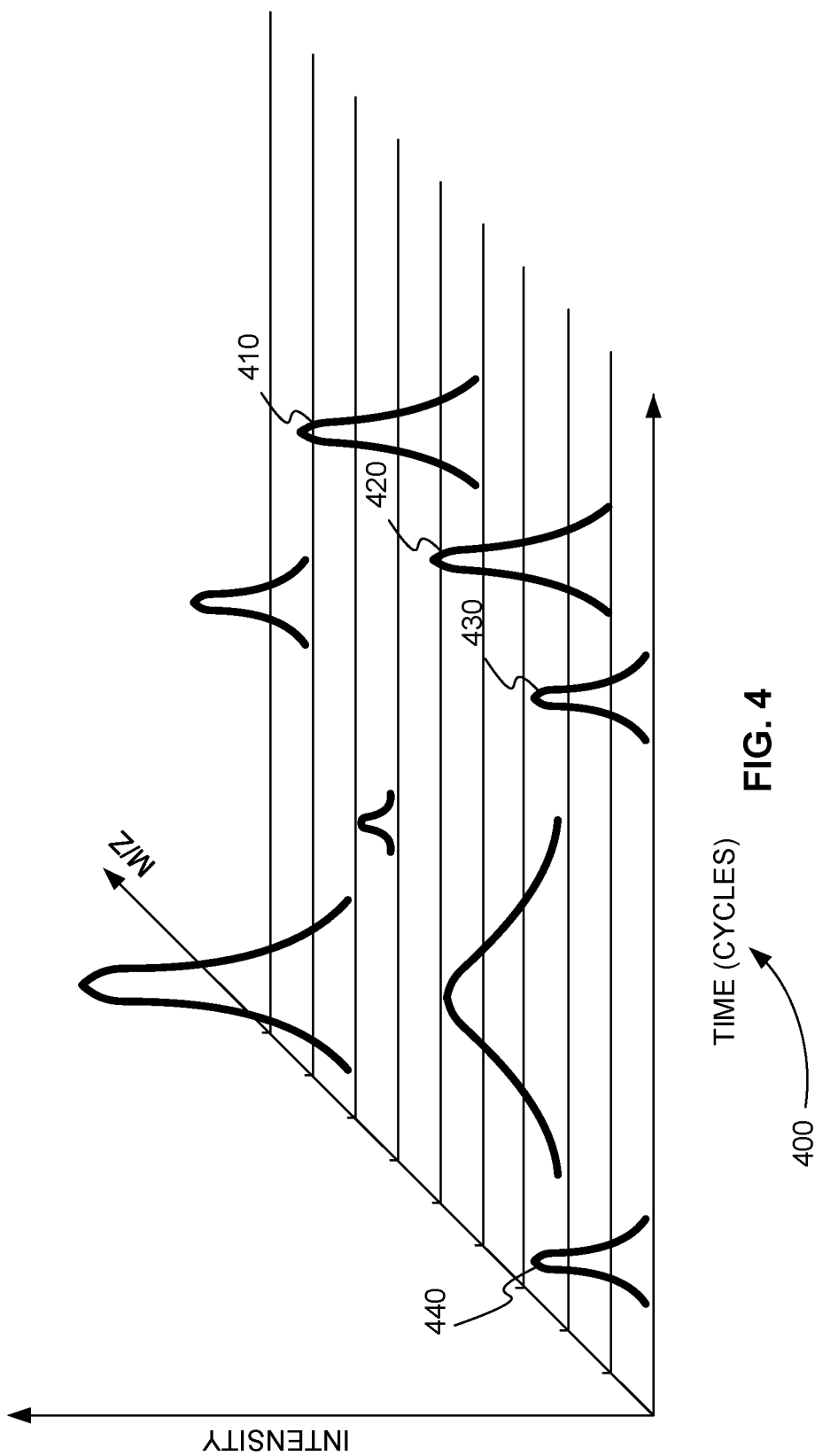
FIG. 4 is an exemplary diagram that shows the three-dimensionality of an XIC obtained for a precursor ion mass selection window over time, in accordance with various embodiments.

FIG. 4 is an exemplary diagram 400 that shows the three-dimensionality of an XIC obtained for a precursor ion mass selection window over time, in accordance with various embodiments. In FIG. 4, the x axis is time or cycle number, the y axis is product ion intensity, and the z axis is m/z. From this three-dimensional plot, more information is obtained.

For example, XIC peaks 410 and 420 both have the same shape and occur at the same time, or same retention time. However, XIC peaks 410 and 420 have different m/z values. This may mean that XIC peaks 410 and 420 are isotopic peaks or represent different product ions from the same precursor ion. If XIC peaks 410 and 420 represent different product ions from the same precursor ion, they can be grouped into an XIC peak group, for example. An XIC peak group is a group of one or more XIC peaks that have the same retention time.

Similarly, XIC peaks 430 and 440 have the same m/z value, but occur at different times. This may mean that XIC peaks 430 and 440 are the same product ion, but they are from two different precursor ions. XIC peaks 430 and 440 show that an accurate retention time is needed to determine the correct product ion XIC peak for each known compound.

After obtaining product ion experimental data using a DIA method, known compounds in a sample are identified by comparing known product ions of a spectral library or theoretical product ions generated from a known compound database to the product ion experimental data. A spectral library includes one or more spectra previously obtained for each known compound in the library. The spectra were obtained for samples that included only one known compound, for example. Theoretical product ions are computationally generated from stored information about the one or more known compounds. This stored information can be stored in many different forms including, but not limited to, databases and flat files.

In various embodiments, stored information about known proteins or peptides is obtained from a FASTA file. The FASTA file is parsed. The proteins parsed from the FASTA file are then computationally digested using the same enzyme used to digest the sample in the experiments. Computational digestion of the one or more known proteins produces one or more theoretical peptides, or one or more peptide precursor ions, for each protein. Theoretical product ions for each protein are obtained by computationally fragmenting theoretical peptide precursor ions of each protein. For example, theoretical product ions are obtained by selecting the b and y fragments of theoretical peptide precursor ions.

As described above, retention time is particularly helpful in identifying known compounds in a DIA experiment, because the product ions in each mass spectrum may be from more than one precursor ion. As a result, it is important that the retention times used to identify known compounds are as accurate as possible.

In various embodiments, after a known compound is identified or quantified in a DIA experiment, a semantic search is performed. For example the name of the identified or quantitated compound is searched against an external database with other Meta data related to the original hypothesis and experimental design. The external database can be, but is not limited to, a database of biological pathways, scientific literature, proteins, protein modifications, or protein functions. Exemplary external database include, but are not limited, to UniProt, BindDB, and STRINGdb.

The semantic search is performed to determine a second hypothesis. The second hypothesis involves, for example, identifying or quantitating one or more additional compounds from the same DIA data and follows the same process of comparing product ion information with spectral libraries or known compound databases.

In various embodiments, the process performing a semantic search for another hypothesis once a compound is identified or quantitated and then confirming or determining the hypothesis by reanalyzing the data to identify or quantitate additional compounds can be performed iteratively to confirm or determine multiple hypotheses.

Figure 5:
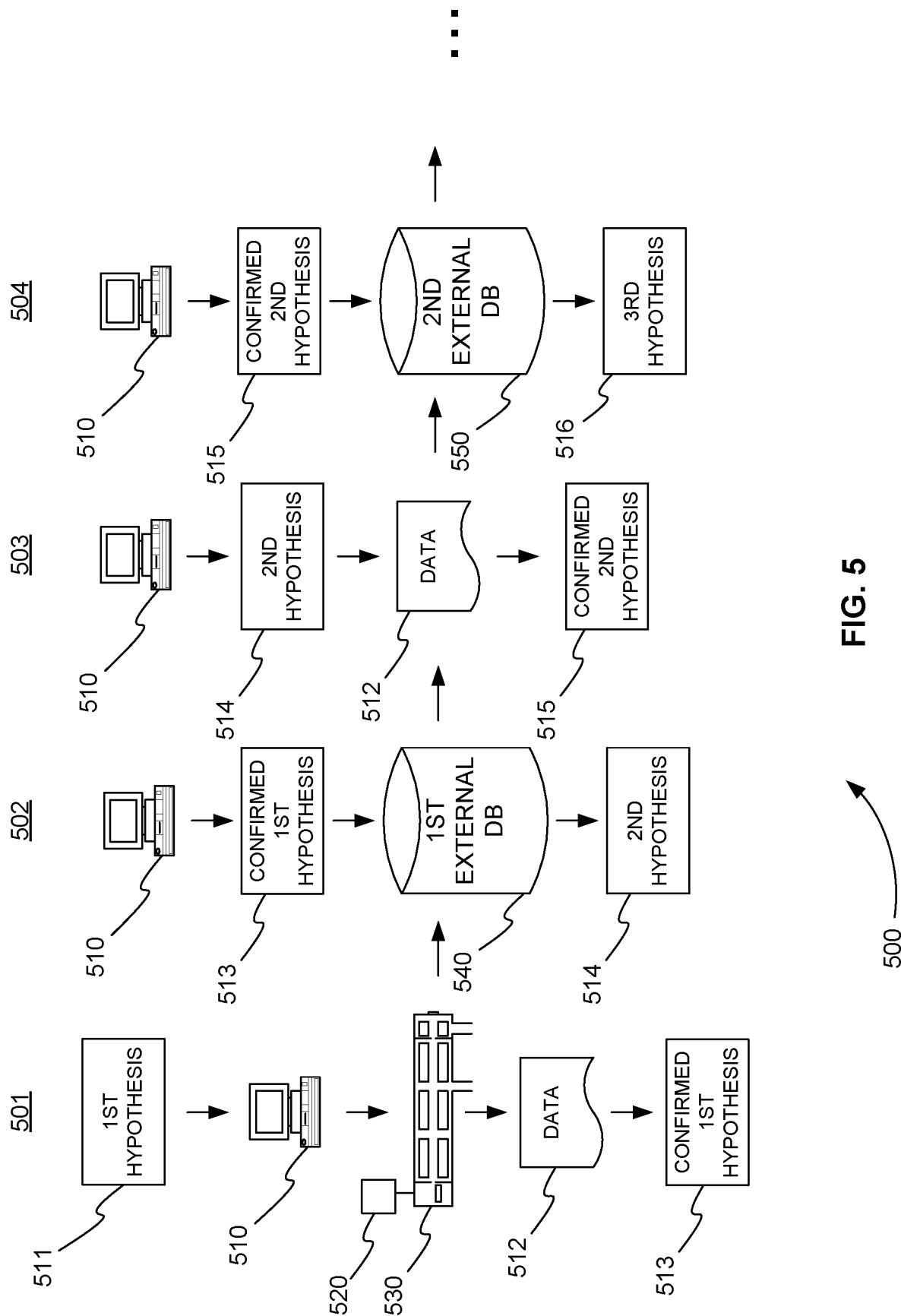
FIG. 5 is an exemplary diagram showing how a semantic search and re-analysis of DIA mass spectrometry data are performed to confirm or determine multiple hypotheses, in accordance with various embodiments.

FIG. 5 is an exemplary diagram 500 showing how a semantic search and re-analysis of DIA mass spectrometry data are performed to confirm or determine multiple hypotheses, in accordance with various embodiments. In step 501, a first hypothesis 511 is selected for a sample (not shown) using processor 510. Processor 510 then analyzes the sample using tandem mass spectrometer 530 and a DIA method. The sample may also be analyzed using separation device 520, for example.

DIA data 512 is produced. Processor 510 confirms first hypothesis 511 using DIA data 512. For example, first hypothesis 511 can be to identify the known compounds from a spectral library in the sample. The known compounds identified in the sample are then confirmed first hypothesis information 513. Confirmed first hypothesis information 513 is, for example, the name of the identified compounds.

In step 502, confirmed first hypothesis information 513 is used to automatically generate second hypothesis 514. Processor 510 searches confirmed first hypothesis information 513 against first external database 540. For example, confirmed first hypothesis information 513 can be the names of identified proteins and first external database 540 can be a database of modified forms of proteins. Second hypothesis 514 is then a list of the matching modified forms of the identified proteins found through a semantic search.

In step 503, processor 510 compares second hypothesis 514 to DIA data 512. For example, if second hypothesis 514 is a list of the matching modified forms of the proteins identified in DIA data 512, DIA data 512 is further analyzed to identify these modified forms. The modified forms that are found are the resulting confirmed second hypothesis information 515.

In step 504, confirmed second hypothesis information 515 is used to automatically generate third hypothesis 516. Step 504 shows that step 502 can be repeatedly iteratively to automatically generate multiple hypotheses that are data dependent. A step similar to step 503 can follow step 504 to confirm third hypothesis 516.

Conventional DIA methods only perform step 501. In order to confirm or determine multiple hypotheses, these methods iteratively rerun step 501. In other words, for each new hypothesis the sample is re-analyzed by tandem mass spectrometer 530. In addition, additional hypotheses are not automatically generated. Each time step 501 is rerun a new hypothesis is manually selected.

System for Automatically Generating Additional Hypotheses

Figure 6:
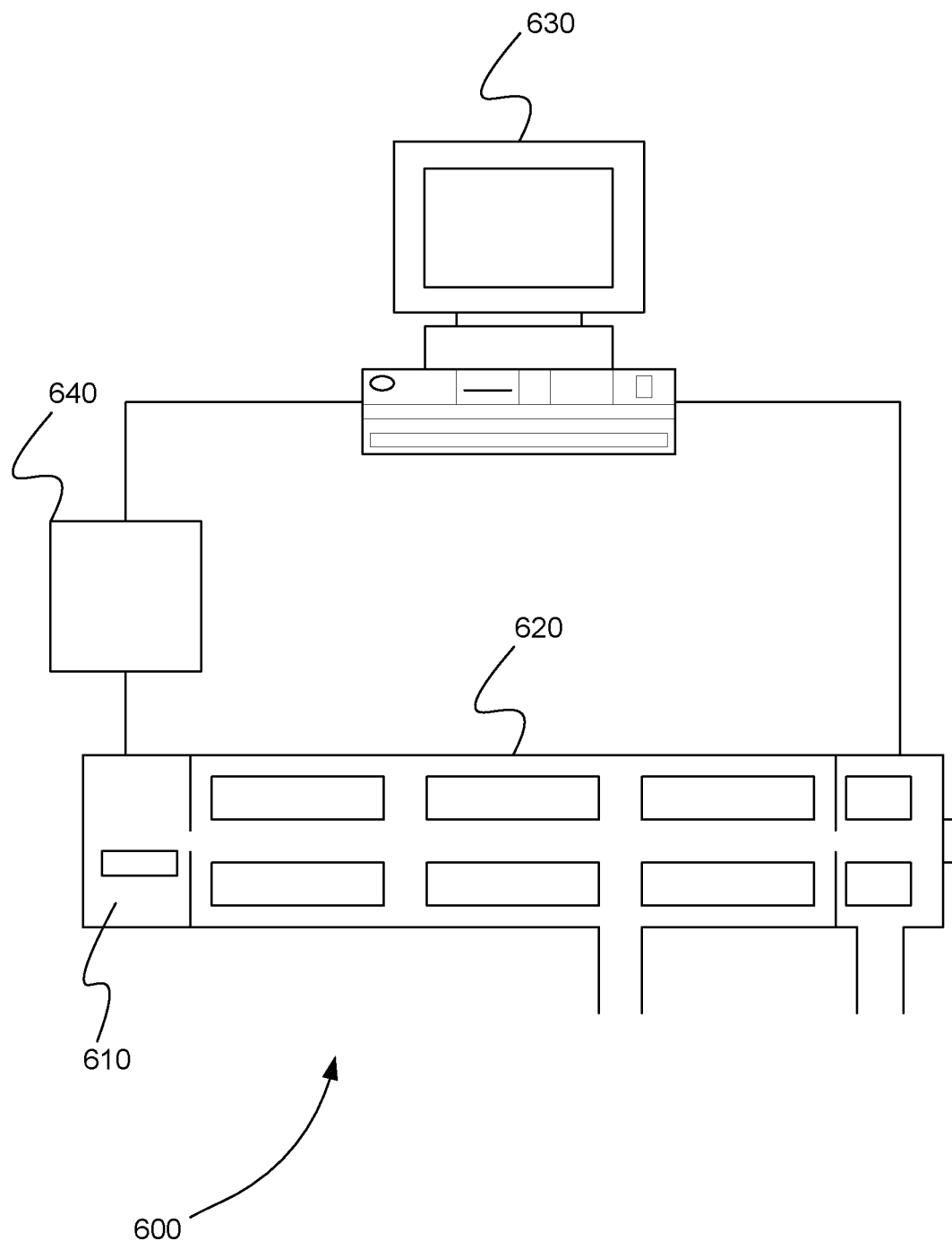
FIG. 6 is a schematic diagram of a system for identifying known compounds of a spectral library in a sample, automatically generating a list of related known compounds, and identifying related known compounds in the sample without reanalyzing the sample using a tandem mass spectrometry DIA method, in accordance with various embodiments.

FIG. 6 is a schematic diagram of a system 600 for identifying known compounds of a spectral library in a sample, automatically generating a list of related known compounds, and identifying related known compounds in the sample without reanalyzing the sample using a tandem mass spectrometry DIA method, in accordance with various embodiments. System 600 includes ion source 610, tandem mass spectrometer 620, and processor 630. In various embodiments, system 600 can also include separation device 640.

Separation device 640 can separate compounds from a sample over time using one of a variety of techniques. These techniques include, but are not limited to, ion mobility, gas chromatography (GC), liquid chromatography (LC), capillary electrophoresis (CE), or flow injection analysis (FIA).

Ion source 610 can be part of tandem mass spectrometer 620, or can be a separate device. Ion source 610 receives the plurality of compounds from separation device 640 and ionizes the plurality of compounds, producing an ion beam of precursor ions.

Tandem mass spectrometer 620 can include, for example, one or more physical mass filters and one or more physical mass analyzers. A mass analyzer of tandem mass spectrometer 620 can include, but is not limited to, a time-of-flight (TOF), quadrupole, an ion trap, a linear ion trap, an orbitrap, or a Fourier transform mass analyzer.

Tandem mass spectrometer 620 receives the ion beam from ion source 610. Tandem mass spectrometer 620 divides an m/z range of the ion beam into two or more precursor ion mass selection windows and selects and fragments the two or more precursor ion mass selection windows during each cycle of a plurality of cycles, producing a plurality of measured product ion spectra.

Processor 630 can be, but is not limited to, a computer, microprocessor, or any device capable of sending and receiving control signals and data from tandem mass spectrometer 620 and processing data. Processor 630 can be, for example, computer system 100 of FIG. 1. In various embodiments, processor 630 is in communication with tandem mass spectrometer 620 and separation device 640.

Processor 630 performs a number of steps. In step (a), processor 630 receives the plurality of measured product ion spectra from tandem mass spectrometer 620. In step (b), processor 630 retrieves from a spectral library of known compounds one or more product ions for each known compound. Alternatively, in various embodiments, processor 630 retrieves a plurality of known compounds from a database. For example, the database can be a protein or peptide database. For each known compound of the database, processor 630 theoretically fragments the known compound, producing one or more theoretical product ions.

In step (c), processor 630 compares the one or more product ions for each known compound to the measured product ion spectra to identify one or more known compounds in the sample. In step (d), processor 630 searches a database of related known compounds using one or more known compounds, producing one or more matching related compounds and one or more product ions for each related compound. Finally, in step (e), processor 630 compares the one or more product ions for each related compound to the measured product ion spectra to identify one or more related compounds in the sample.

In various embodiments, one or more product ions are produced for each related compound by retrieving from a spectral library of related compounds one or more product ions for each related compound. Alternatively, in various embodiments, one or more product ions are produced for each related compound by theoretically fragmenting each related compound of the one or more matching related compounds.

Figure 7:
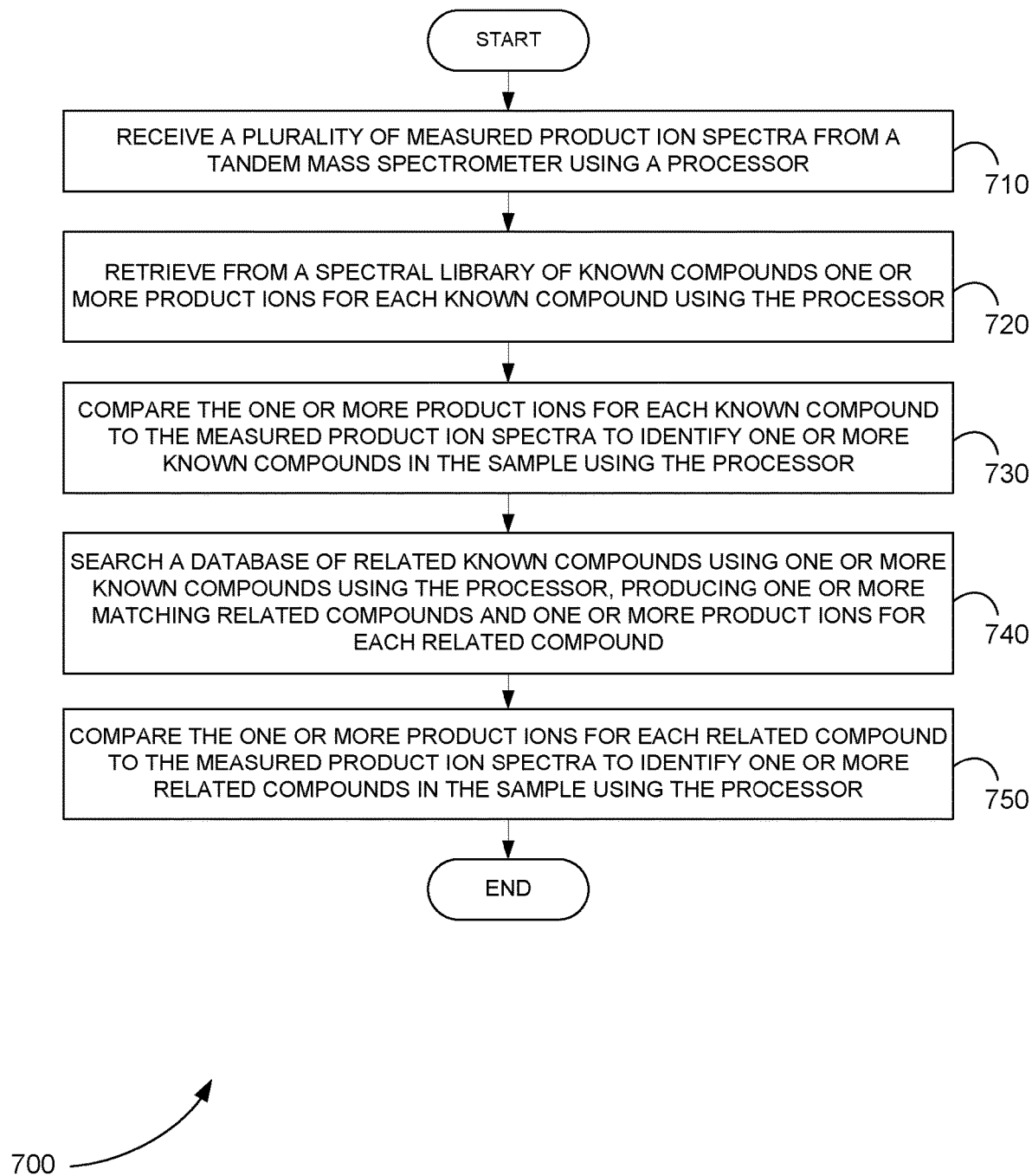
FIG. 7 is a flowchart showing a method for identifying known compounds of a spectral library in a sample, automatically generating a list of related known compounds, and identifying related known compounds in the sample without reanalyzing the sample using a tandem mass spectrometry DIA method, in accordance with various embodiments.

Method for Automatically Generating Additional Hypotheses Using a Spectral Library FIG. 7 is a flowchart showing a method 700 for identifying known compounds of a spectral library in a sample, automatically generating a list of related known compounds, and identifying related known compounds in the sample without reanalyzing the sample using a tandem mass spectrometry DIA method, in accordance with various embodiments.

In step 710 of method 700, a plurality of measured product ion spectra are received from a tandem mass spectrometer using a processor. The plurality of measured product ion spectra are produced by the tandem mass spectrometer by dividing an m/z range of an ion beam into two or more precursor ion mass selection windows and selecting and fragmenting the two or more precursor ion mass selection windows during each cycle of a plurality of cycles. The ion beam is produced by an ion source that ionizes a plurality of compounds, producing an ion beam of precursor ions. The plurality of compounds are separated from a sample by a separation device.

In step 720, one or more product ions for each known compound are retrieved from a spectral library of known compounds using the processor.

In step 730, the one or more product ions for each known compound are compared to the measured product ion spectra to identify one or more known compounds in the sample using the processor.

In step 740, a database of related known compounds is searched using one or more known compounds using the processor, producing one or more matching related compounds and one or more product ions for each related compound.

In step 750, the one or more product ions for each related compound are compared to the measured product ion spectra to identify one or more related compounds in the sample using the processor.

Method for Automatically Generating Additional Hypotheses Using a Database

Figure 8:
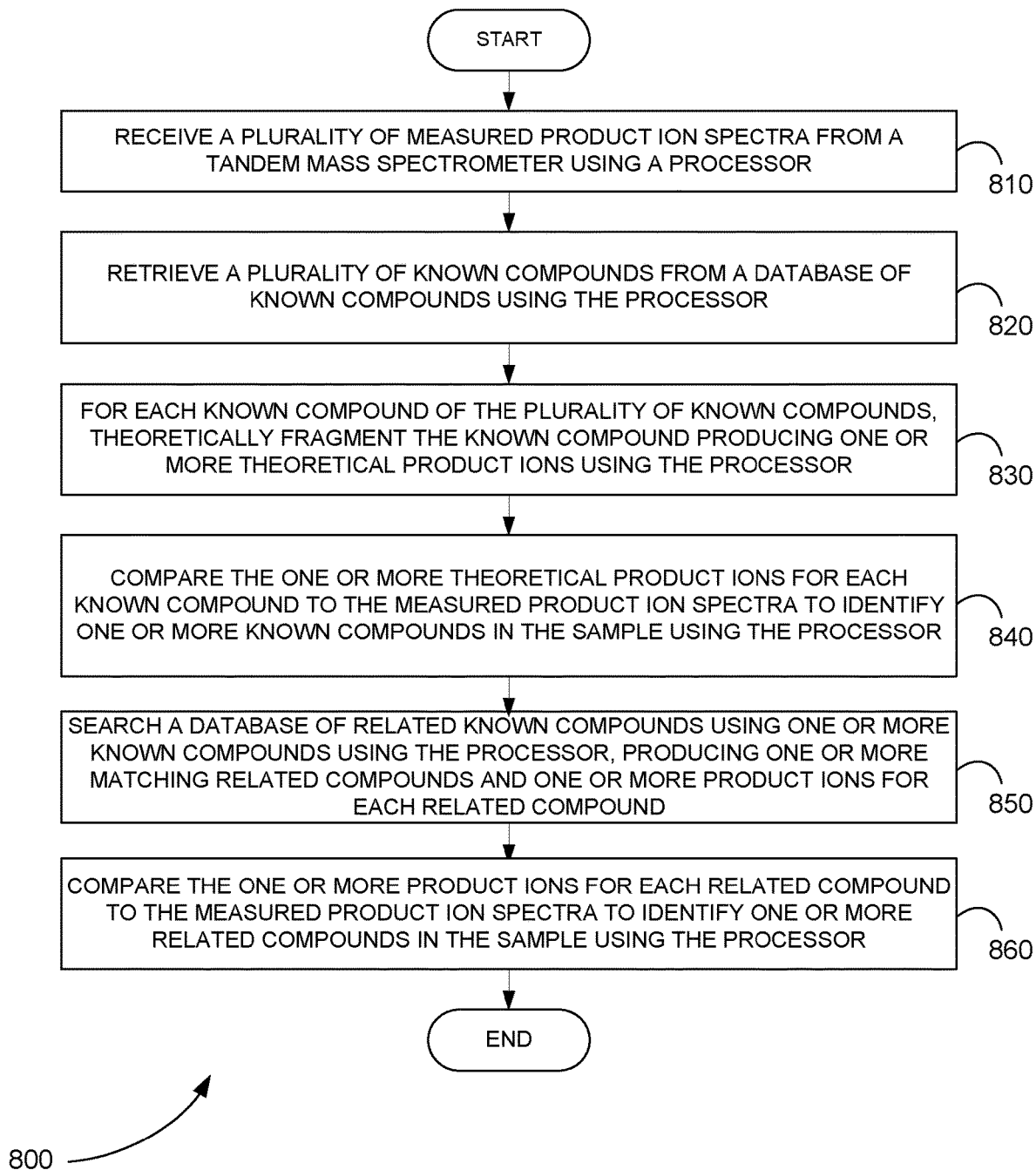
FIG. 8 is a flowchart showing a method for identifying known compounds from a database of known compounds in a sample, automatically generating a list of related known compounds, and identifying related known compounds in the sample without reanalyzing the sample using a tandem mass spectrometry DIA method, in accordance with various embodiments.

FIG. 8 is a flowchart showing a method 800 for identifying known compounds from a database of known compounds in a sample, automatically generating a list of related known compounds, and identifying related known compounds in the sample without reanalyzing the sample using a tandem mass spectrometry DIA method, in accordance with various embodiments.

In step 810 of method 800, a plurality of measured product ion spectra are received from a tandem mass spectrometer using a processor. The plurality of measured product ion spectra are produced by the tandem mass spectrometer by dividing an m/z range of an ion beam into two or more precursor ion mass selection windows and selecting and fragmenting the two or more precursor ion mass selection windows during each cycle of a plurality of cycles. The ion beam is produced by an ion source that ionizes a plurality of compounds, producing an ion beam of precursor ions. The plurality of compounds are separated from a sample by a separation device.

In step 820, a plurality of known compounds are retrieved from a database of known compounds using the processor.

In step 830, for each known compound of the plurality of known compounds, the known compound is theoretically fragmented producing one or more theoretical product ions using the processor.

In step 840, the one or more theoretical product ions for each known compound are compared to the measured product ion spectra to identify one or more known compounds in the sample using the processor.

In step 850, a database of related known compounds is searched using one or more known compounds using the processor, producing one or more matching related compounds and one or more product ions for each related compound.

In step 860, the one or more product ions for each related compound are compared to the measured product ion spectra to identify one or more related compounds in the sample using the processor.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for identifying known compounds of a spectral library in a sample, automatically generating a list of related known compounds, and identifying related known compounds in the sample without reanalyzing the sample using a tandem mass spectrometry data independent acquisition (DIA) method, comprising:
   a separation device that separates a plurality of compounds from a sample over time;
   an ion source that receives the plurality of compounds from the separation device and ionizes the plurality of compounds, producing an ion beam of precursor ions;
   a tandem mass spectrometer that receives the ion beam, divides a mass-to-charge ratio (m/z) range of the ion beam into two or more precursor ion mass selection windows, and selects and fragments the two or more precursor ion mass selection windows during each cycle of a plurality of cycles, producing a plurality of measured product ion spectra; and
   a processor in communication with the tandem mass spectrometer that
      (a) receives the plurality of measured product ion spectra from the tandem mass spectrometer,
      (b) retrieves from a spectral library of known compounds one or more product ions for each known compound,
      (c) compares the one or more product ions for each known compound to the measured product ion spectra to identify one or more known compounds in the sample,
      (d) performs a semantic search of a database of related known compounds using names of the identified one or more known compounds, producing one or more matching related compounds and one or more product ions for each related compound, and
      (e) compares the one or more product ions for each related compound to the measured product ion spectra to identify one or more related compounds in the sample.

2. The system of claim 1, wherein one or more product ions are produced for each related compound by retrieving from a spectral library of related compounds one or more product ions for each related compound.

3. The system of claim 1, wherein one or more product ions are produced for each related compound by theoretically fragmenting each related compound of the one or more matching related compounds.

4. A system for identifying known compounds from a database of known compounds in a sample, automatically generating a list of related known compounds, and identifying related known compounds in the sample without reanalyzing the sample using a tandem mass spectrometry data independent acquisition (DIA) method, comprising:
   a separation device that separates a plurality of compounds from a sample over time;
   an ion source that receives the plurality of compounds from the separation device and ionizes the plurality of compounds, producing an ion beam of precursor ions;
   a tandem mass spectrometer that receives the ion beam, divides a mass-to-charge ratio (m/z) range of the ion beam into two or more precursor ion mass selection windows, and selects and fragments the two or more precursor ion mass selection windows during each cycle of a plurality of cycles, producing a plurality of measured product ion spectra; and
   a processor in communication with the tandem mass spectrometer that
      (a) receives the plurality of measured product ion spectra from the tandem mass spectrometer,
      (b) retrieves a plurality of known compounds from a database of known compounds,
      (c) for each known compound of the plurality of known compounds, theoretically fragments the known compound producing one or more theoretical product ions,
      (d) compares the one or more theoretical product ions for each known compound to the measured product ion spectra to identify one or more known compounds in the sample,
      (e) performs a semantic search of a database of related known compounds using names of the identified one or more known compounds, producing one or more matching related compounds and one or more product ions for each related compound, and
      (f) compares the one or more product ions for each related compound to the measured product ion spectra to identify one or more related compounds in the sample.

5. The system of claim 4, wherein one or more product ions are produced for each related compound by retrieving from a spectral library of related compounds one or more product ions for each related compound.

6. The system of claim 4, wherein one or more product ions are produced for each related compound by theoretically fragmenting each related compound of the one or more matching related compounds.

7. A method for identifying known compounds of a spectral library in a sample, automatically generating a list of related known compounds, and identifying related known compounds in the sample without reanalyzing the sample using a tandem mass spectrometry data independent acquisition (DIA) method, comprising:
   (a) receiving a plurality of measured product ion spectra from a tandem mass spectrometer using a processor,
      wherein the plurality of measured product ion spectra are produced by the tandem mass spectrometer by dividing a mass-to-charge ratio (m/z) range of an ion beam into two or more precursor ion mass selection windows and selecting and fragmenting the two or more precursor ion mass selection windows during each cycle of a plurality of cycles,
      wherein the ion beam is produced by an ion source that ionizes a plurality of compounds, producing an ion beam of precursor ions, and
      wherein the plurality of compounds are separated from a sample by a separation device;
   (b) retrieving from a spectral library of known compounds one or more product ions for each known compound using the processor;
   (c) comparing the one or more product ions for each known compound to the measured product ion spectra to identify one or more known compounds in the sample using the processor;

(d) performing a semantic search of a database of related known compounds using names of the identified one or more known compounds using the processor, producing one or more matching related compounds and one or more product ions for each related compound; and (e) comparing the one or more product ions for each related compound to the measured product ion spectra to identify one or more related compounds in the sample using the processor.

8. The method of claim 7, wherein one or more product ions are produced for each related compound by retrieving from a spectral library of related compounds one or more product ions for each related compound.

9. The method of claim 7, wherein one or more product ions are produced for each related compound by theoretically fragmenting each related compound of the one or more matching related compounds.

* * * * *